United States Patent [19]

Buckley et al.

[11] Patent Number: 4,524,868

[45] Date of Patent: Jun. 25, 1985

[54] CARRYING CASE FOR PRE-DRAWN SYRINGE

[76] Inventors: Damon S. Buckley; Marlene E. Buckley, both of R.D. 3, Box 3025, Stroudsburg, Pa. 18360

[21] Appl. No.: 238,375

[22] Filed: Feb. 26, 1981

[51] Int. Cl.³ .............................................. B65D 85/10
[52] U.S. Cl. ..................................... 206/364; 206/523
[58] Field of Search ........................ 206/523, 524, 364

[56] References Cited

U.S. PATENT DOCUMENTS

| 630,638 | 8/1899 | Tatum | 206/364 |
| 4,093,010 | 6/1978 | Hunley et al. | 206/523 |
| 4,254,862 | 3/1981 | Barratt | 229/44 R |

FOREIGN PATENT DOCUMENTS

| 1210324 | 3/1960 | France | 206/523 |
| 1341968 | 9/1963 | France | 206/523 |
| 856558 | 12/1960 | United Kingdom | 206/523 |
| 1103584 | 2/1968 | United Kingdom | 206/523 |

*Primary Examiner*—Joseph Man-Fu Moy
*Attorney, Agent, or Firm*—Ruth Moyerman

[57] ABSTRACT

A carrying case for a pre-drawn hypodermic syringe is disclosed. The carrying case is constructed of a flexible, resilient material and includes a liner made of an elastic material such as foamed polyester. The liner includes a cutout portion adapted to cradle a pre-drawn and capped syringe. The overall case is of a size and dimension only slightly larger than the syringe itself and is intended to be carried in the purse or the pocket of a diabetic to be used for the injection of insulin.

In use, the syringe is extracted from the case by the user applying his thumbs to deform the lining and casing, and cause the syringe to pop up so that it may be readily grasped.

2 Claims, 2 Drawing Figures

CARRYING CASE FOR PRE-DRAWN SYRINGE

BACKGROUND OF THE INVENTION

1. Field of the Invention

This invention relates to special receptacles or packaging, and more particularly to syringes.

2. Description of the Prior Art

The packaging art for syringes is both old and extensive. Carrying cases for syringes begin at least as early as U.S. Pat. No. 405,100 to Kloppe and U.S. Pat. No. 2,421,495 to Green, both of which utilize glass casing, up to U.S. Pat. No. 3,058,584 to Marshall and U.S. Pat. No. 3,642,123 to Knox which are multipurpose carrying cases including a lot of paraphernalia. Multiple disposable packages are also known. For example U.S. Pat. No. 3,008,570 to Roehr, et al.; U.S. Pat. No. 3,372,798 to Thomas; U.S. Pat. No. 3,746,155 to Seeley and U.S. Pat. No. 4,214,659 to Jaeschke, et al. are all examples of the disposable syringe package.

Notwithstanding the foregoing references, and probably others in the art, there has remained a need for a specific case designed to be utilized by the diabetic. The diabetic has unique problems in that he or she must eat within thirty minutes from the time of injection. This presents a problem in modern times where traveling, especially by air, and other situations where there is an uncertain meal time become more numerous. It is extremely awkward, inconvenient and sometimes impossible for the diabetic to fumble with insulin bottles and try to draw a syringe in, for example, an airline toilet where the small space and vibrations of the moving plane conspire to make this life saving exercise next to impossible to perform.

To save themselves time and also to provice convenience and stability to those who are elderly or clumsy, it is highly desirable that the diabetic be able to pre-draw a syringe with the correct amount of insulin, cap the needle and store the syringe so that it will be both protected but remain easily accessible.

The foregoing prior art references are not addressed to this problem in as much as a disposable syringe package is intended for a doctor's office and is customarily not a pre-drawn syringe. The older or other prior art carrying cases are totally unadaptable to the modern times and to the need for a portable carrying case which may be easily transported in the pocket or pocketbook of the user.

There is therefore a great need for a totally new approach for cases for syringes, particularly pre-drawn syringes for diabetics. A case is needed which is small, easy to open, allows a syringe to be withdrawn with facility, readily reusable, and inexpensive to manufacture.

SUMMARY OF THE INVENTION

The aforementioned prior art problems are overcome by the carrying case for pre-drawn hypodermic syringes of this invention.

The carrying case of this invention is generally parallel-pipedal casing made of a flexible, resilient material such as XICERO PVC Vinyl. The carrying case is preferably only slightly larger than the pre-drawn syringe for which it is designed and is thus highly portable, adapting itself even to be contained in the vest or shirt pocket of a man. Extra rigidity for the case may be achieved by use of cardboard or the like inserted between an inner and outer casing wall. The casing contains a liner and the material of the liner must also be made of an elastic material, preferably a cellular elastic material such as foamed polyester. The liner totally fills the carrying case with the exception of a cutout, or aperture, portion which is predetermined to match almost exactly the contours of the pre-drawn syringe.

The pre-drawn and capped syringe may thus be cradled or snuggly fit in the liner and a cover for the casing closed over the liner and its contents.

The advantage, a unique feature of this invention, is that it allows the user to withdraw the syringe by opening the cover and with the pressure of the hands, particularly the thumbs, the lining and casing may be withdrawn away from the syringe causing the syringe to either pop up or to display a sufficiently prominent section that the user may grasp the body of the syringe and readily extract it from the case.

It is therefore an object of this invention to provide a carrying case for a pre-drawn syringe which is truly easy to use, even by the elderly, those with limited dexterity, and the ill.

It is yet a further object of this invention to provide a carrying case for a pre-drawn syringe which is truly portable, being compact in size, unobtrusive in appearance and adaptable to fit the ordinary pocket or pocketbook.

It is yet another object of this invention to provide a truly versatile carrying case, one which is adaptable to the syringes of all the conventional manufacturers.

It is still another object of this invention to provide the aforementioned syringe in a simplicity of design such that its manufacture is inexpensive, thus putting the syringe carrying case within the price range of the population in general.

These and other objects will be more readily ascertainable to one skilled in the art by a consideration of the following drawing and exemplary embodiments.

BRIEF DESCRIPTION OF THE DRAWING(S)

FIG. 1 shows an elevation of the preferred embodiment of the carrying case of this invention.

FIG. 2 also shows the preferred embodiment of this invention to illustrate its use.

DETAILED DESCRIPTION OF THE PREFERRED EMBODIMENT(S)

Figure 1:
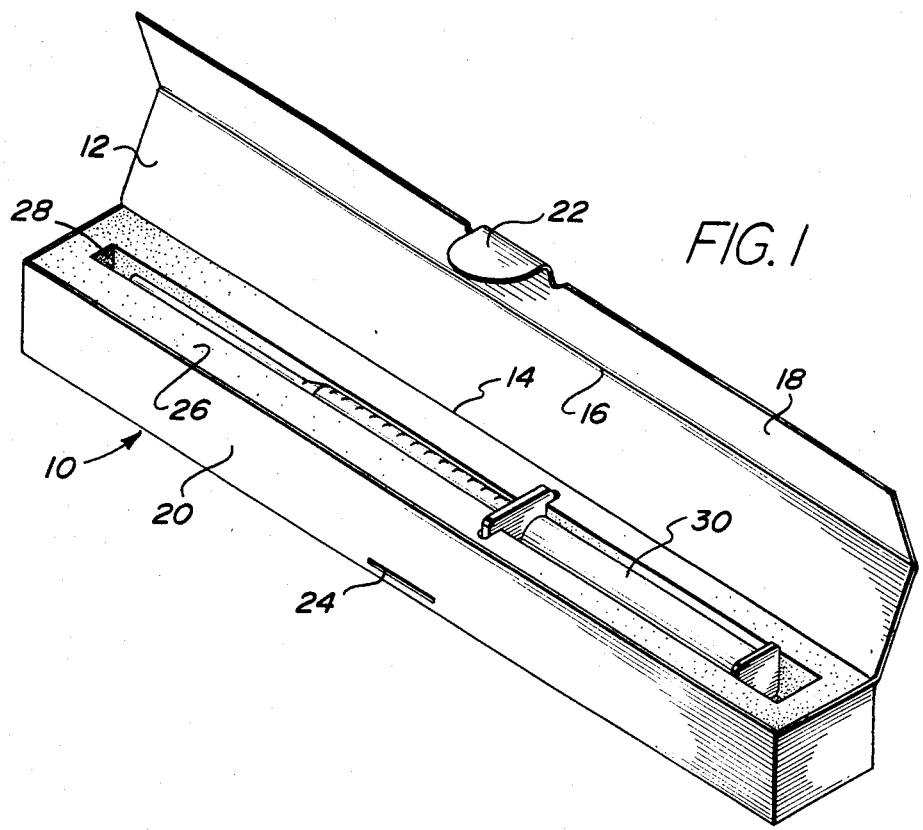

Referring now to the drawings and more particularly to FIG. 1, a preferred embodiment of the carrying case of this invention is shown including a drawn syringe. The carrying case includes casing 10 made of a flexible plastic such as XICERO PVC Vinyl, and which is generally parallelpipedal in configuration. An integral cover 12 is shown hingedly attached along edge 14 of carrying case 10. It is preferable to make cover 12 as an integral part of casing 10 and the hinge portion is formed merely by the bending of cover 12 at edge 14. Cover 12 also includes fold 16 midwat its length thereby allowing the flap portion 18 to be generated. When the case is closed, flap portion 18 overlaps casing side 20 and detent portion 22 slides into casing 10 along slit 24 at the edge of side 20. Liner 26 is shown shaped to fit snuggly within casing 10. Liner 26 includes aperature 28 whose cross section is generally that of syringe 30. Liner 26 is preferably made of an elastic, cellular material such as foamed polyester to provide a liner which is simulatneously easily deformable and elastic in nature so that the shape returns.

Figure 2:
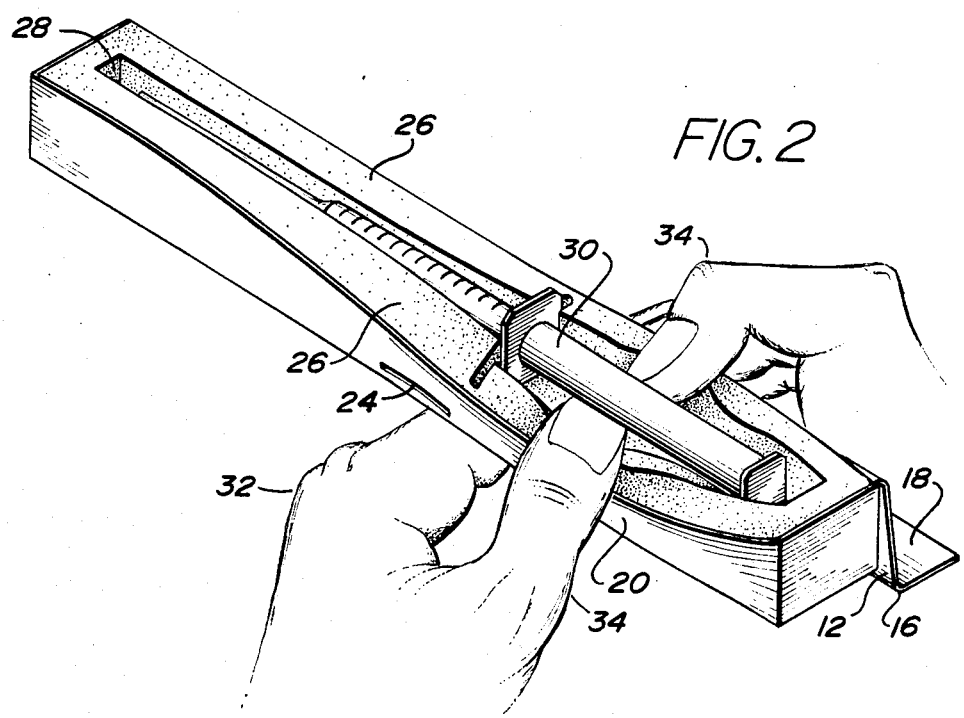

Referring now to FIG. 2, the carrying case of this invention is shown in use. The hands of the user are indicated at 32 and it may be readily seen in FIG. 2 that as thumbs 34 encounter liner 26 and casing edge 20, these parts are susceptible to manual deformation, a step which causes syringe 30 to be exposed and easily available for grasping by one of the user's hands.

The carrying case of this invention has many advantages. Chiefly, there is now provided an inexpensive, easy to use, lightweight portable carrying case for a pre-drawn syringe to allow the diabetic to function better within and cope with the demands of modern living. Where before there was no means to easily transport a pre-drawn syringe, now by the use of the carrying case of this invention, one may, by the use of both—or even one hand—cause the syringe to pop up to be used and returned to its case for later reloading and reuse.

The utility of the carrying case of this invention is applicable to old and young, handicapped as well as normal, and all within a price range to make it truly universal.

Having now described and illustrated my invention, it is not intended that such description limit the scope of this invention, but rather that this invention be limited only by reasonable interpretation of the apended claims.

What is claimed is:

1. A carrying case for a pre-drawn syringe comprising:
    (a) a generally parallelpipedal casing, said casing being made of deformable, pliant, resilient material of construction;
    (b) an integral cover hingedly attached to said casing, said cover including a mid sction fold to provide an overlap portion for one face of said casing, said cover also including means to releasably secure said cover to said casing; and,
    (c) a liner fitted within said casing, said liner contoured to fill said casing, at least one shaped aperture generally conforming in cross section to that of a drawn syringe to permit a syringe to be sunken therein, said aperture's distance from said casing being generally only wide enough to allow a user's thumb to span the distance, said liner consisting of a cellular, elastic material of construction so that a syringe resting in said aperture, snugly held, may be removed therefrom by a gentle simultaneously manual flexing of said casing and a deformation of said liner to separate said syringe from said liner to thereby expose and make prominent a portion of the syringe to facilitate its grasping and removal thereof by the user.

2. The carrying case according to claim 1 wherein there is a single aperture.

* * * * *